(12) United States Patent
Gubbini et al.

(10) Patent No.: US 9,980,700 B2
(45) Date of Patent: May 29, 2018

(54) ULTRASOUND APPARATUS COVER

(75) Inventors: Alessandro Gubbini, State College, PA (US); Bradley Nelson, Boalsburg, PA (US)

(73) Assignee: Sound Technology, Inc., State College, PA (US)

( * ) Notice: Subject to any disclaimer, the term of this patent is extended or adjusted under 35 U.S.C. 154(b) by 348 days.

(21) Appl. No.: 14/234,063

(22) PCT Filed: Jul. 22, 2011

(86) PCT No.: PCT/US2011/044798
§ 371 (c)(1),
(2), (4) Date: Jan. 21, 2014

(87) PCT Pub. No.: WO2013/015769
PCT Pub. Date: Jan. 31, 2013

(65) Prior Publication Data
US 2014/0163382 A1    Jun. 12, 2014

(51) Int. Cl.
*A61B 8/00*    (2006.01)

(52) U.S. Cl.
CPC .......... *A61B 8/4422* (2013.01); *A61B 8/4281* (2013.01); *A61B 8/4455* (2013.01)

(58) Field of Classification Search
CPC combination set(s) only.
See application file for complete search history.

(56) References Cited

U.S. PATENT DOCUMENTS

| 4,617,239 A | * | 10/1986 | Maruyama | B41M 5/443 428/452 |
| 5,722,412 A | * | 3/1998 | Pflugrath | A61B 8/00 600/441 |
| 5,738,099 A | | 4/1998 | Chang | |

(Continued)

FOREIGN PATENT DOCUMENTS

| JP | 2011083363 | 4/2011 |
| WO | 96-25888 | 8/1996 |
| WO | 2008024515 A2 | 2/2008 |

OTHER PUBLICATIONS

Japanese Office Action dated Apr. 28, 2015 for Japanese Application No. 2014-522794.

(Continued)

*Primary Examiner* — Serkan Akar
*Assistant Examiner* — Farshad Negarestan
(74) *Attorney, Agent, or Firm* — Anthony M. Del Zoppo, III; Driggs, Hogg, Daugherty & Del Zoppo, Co., LPA

(57) ABSTRACT

An ultrasound transducer cover (100) includes a base (202), including an acoustically transmissive membrane (110) with first and second opposing sides. The cover further includes walls (204, 206) protruding from the base in a same direction away from the first side of the base, forming a cavity about the acoustically transmissive membrane with a geometry that conforms to a geometry of a probe head of an ultrasound apparatus housing a transducer array and a corresponding acoustic window. The cover further includes an acoustically transmissive adhesive (108) disposed on the (Continued)

membrane in the cavity, wherein the acoustically transmissive adhesive maintains the cover on the ultrasound apparatus in response to installing the cover on the ultrasound apparatus.

21 Claims, 6 Drawing Sheets

(56) References Cited

U.S. PATENT DOCUMENTS

| | | | |
|---|---|---|---|
| 5,817,024 A | | 10/1998 | Ogle et al. |
| 6,048,323 A | * | 4/2000 | Hon ................. A61B 5/4356 |
| | | | 600/588 |
| 6,132,378 A | | 10/2000 | Marino |
| 6,719,699 B2 | | 4/2004 | Smith |
| 2003/0149359 A1 | | 8/2003 | Smith |
| 2006/0030778 A1 | | 2/2006 | Mendlein et al. |
| 2006/0264751 A1 | | 11/2006 | Wendelken et al. |
| 2007/0276241 A1 | * | 11/2007 | Park ..................... A61B 8/00 |
| | | | 600/437 |
| 2010/0036257 A1 | | 2/2010 | Sano et al. |

OTHER PUBLICATIONS

International search report for PCT/IB2011/044978 published as WO 2013/015769 A1.

Bio-Medical Instruments, Inc., 2387 East 8 Mile Road, Warren, MI 48091-2486; bio-medical.com/products/Aquasonic 100 Sterile—48 Overwrapped Foil Pouches.

* cited by examiner

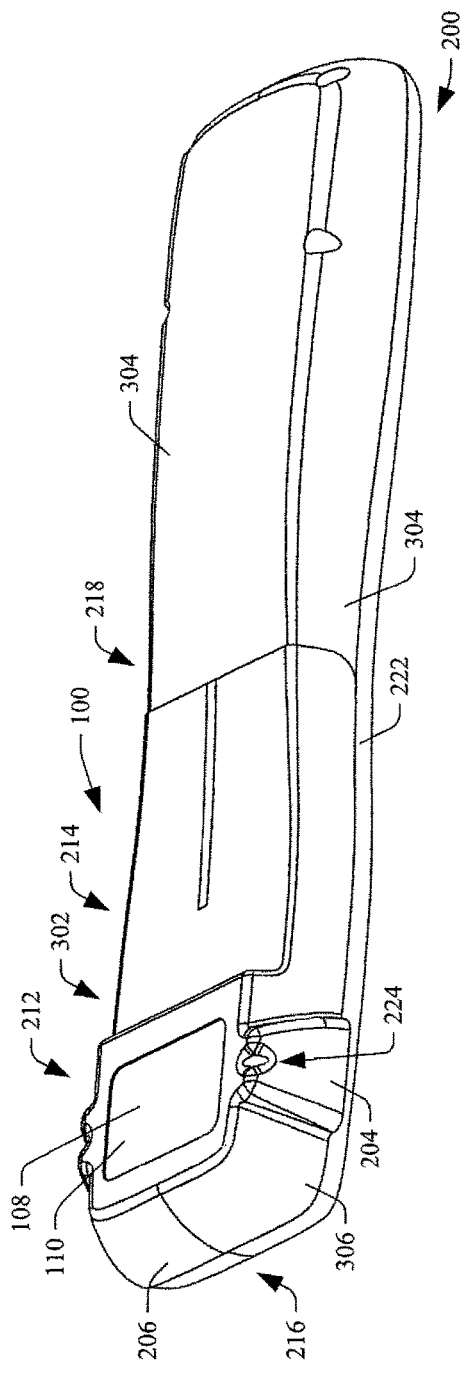
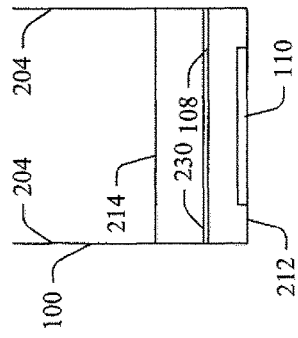
FIGURE 3
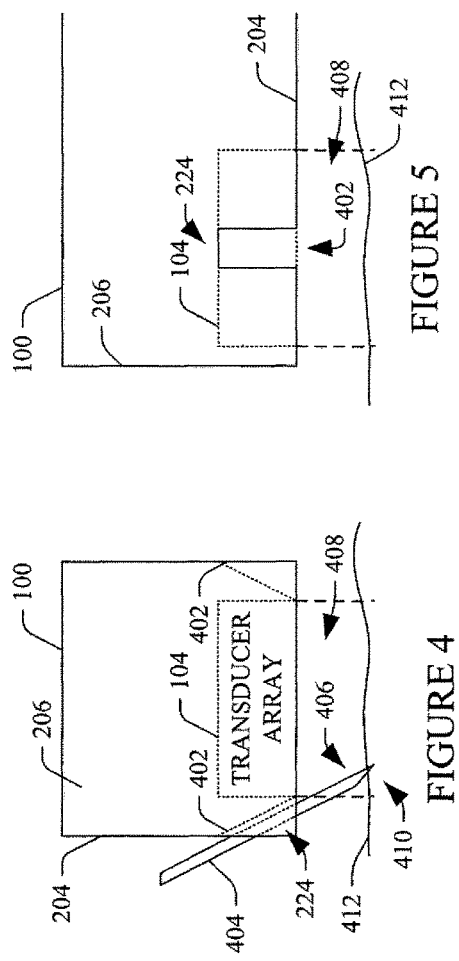
FIGURE 4
FIGURE 5
FIGURE 6

ULTRASOUND APPARATUS COVER

RELATED APPLICATION

This application is a national filing of PCT application Serial No. PCT/US2011/044978, filed Jul. 22, 2011, published as WO2013/015769 on Jan. 31, 2013. This application claims priority to PCT application Serial No. PCT/US2011/044978, published as WO2013/015769 on Jan. 31, 2013.

TECHNICAL FIELD

The following generally relates to ultrasound imaging and more particularly to a medical ultrasound transducer array cover.

BACKGROUND

Ultrasound scanners provide useful information about the interior characteristics of an object under examination. In medical applications, clinicians have used ultrasound scanners to examine human subjects in settings such as hospitals, physician's offices, and other locations. Ultrasound scanners have been used in the emergency room, operating room, radiology department, patient room, and/or other environments. In use, an acoustic coupling agent, typically a lubricious gel largely composed of water and propylene glycol, is placed on the acoustic window/lens of the ultrasound transducer array and/or an area of the patient in connection with the region of interest to be scanned. The user then positions the transducer array with respect to the area of the patient. The gel between the acoustic window and the area provides an acoustic medium that facilitates transferring ultrasound signals there between. The ultrasound scanner can then be used to scan the region of interest.

In some environments (e.g., sterile environments), transducer covers are used. Transducer covers conventionally have included a rubber or thin plastic bag or sheath that physically surrounds and encloses the entire or a sub-portion of the probe. When a cover is used an acoustic coupling agent is required both between the transducer and cover and between the cover and the patient. Such covers are supplied sterilized in sterile packaging (e.g., U.S. Pat. No. 3,754,700) and may come prefilled with a coupling gel and/or other coupling agent. Other covers are not pre-filled, and the user adds gel into the bag prior installing on the transducer. The user also applies the gel on the outside of the cover and/or on the area of the patient. Other covers have included cup-shaped covers that snap on the probe (e.g., U.S. Pat. No. 6,132,378) and self-adhesive thin pliable film dressings that are wrapped around and adhere to the probe (e.g., U.S. 2006/0264751 A1). Unfortunately, such covers can be cumbersome to install and use.

Procedures such as biopsies, peripheral intravenous insertions (PIVs), and/or other procedures which involve use of a needle entail employing a separate needle guide apparatus with the probe or a needle guide accessory that attaches to the probe. Generally, such needle guides have been configured to constrain a needle in a fixed path (plane and/or insertion angle), for example, that is in the middle of elevation of the acoustic beam (traditional single plane transducer) represented by a guide line on the ultrasound system. A typical needle guide has two main components: a reusable bracket that snaps on the probe and is placed under the cover (where a cover is used), and a disposable guide that attaches from outside the cover. Unfortunately, such assembly may not be easy to install and may require more than one person to maintain sterility during cover and/or needle guide installation in a sterile environment, and may be too restrictive for PIV. Furthermore, for certain procedures such as peripheral intravenous insertions, the size of the sterile field is limited to a small area directly around the insertion site and a cover that encloses the entire transducer may provide more coverage than is required. Moreover, traditional ultrasound gel is not well-suited for ultrasound guided peripheral intravenous insertions, for example, because of post needle insertion cleanup in preparation for application of dressings over the catheter.

SUMMARY

Aspects of the application address the above matters, and others.

In one aspect, an ultrasound transducer cover includes a base, including an acoustically transmissive membrane with first and second opposing sides. The cover further includes walls protruding from the base in a same direction away from the first side of the base, forming a cavity about the acoustically transmissive membrane with a geometry that conforms to a geometry of a probe head an ultrasound apparatus housing a transducer array and a corresponding acoustic window. The cover further includes an acoustically transmissive adhesive disposed on the base in the cavity. The acoustically transmissive adhesive maintains the cover on the ultrasound apparatus in response to installing the cover on the ultrasound apparatus.

In another aspect, a method includes obtaining an ultrasound transducer cover. The cover includes a base with an acoustically transmissive membrane with first and second opposing sides. The cover further includes walls protruding from the base in a same direction away from the first side of the base, forming a cavity about the acoustically transmissive membrane with a geometry that conforms to a geometry of a probe head an ultrasound apparatus housing a transducer array and a corresponding acoustic window. The cover further includes an acoustically transmissive adhesive disposed on the base in the cavity. The cover further includes an adhesive liner removeably affixed to the acoustically transmissive adhesive. The method further includes removing the adhesive liner from the acoustically transmissive adhesive. The method further includes installing the cover on the probe head by physically contacting the acoustically transmissive adhesive with the acoustically transmissive window of the ultrasound apparatus. The acoustically transmissive adhesive maintains the cover on the ultrasound apparatus in response to installing the cover on the ultrasound apparatus.

In another aspect, a method includes obtaining an ultrasound transducer cover. The cover includes a base with an acoustically transmissive membrane with first and second opposing sides. The cover further includes walls protruding from the base in a same direction away from the first side of the base, forming a cavity about the acoustically transmissive membrane with a geometry that conforms to a geometry of a probe head an ultrasound apparatus housing a transducer array and a corresponding acoustic window. The cover further includes an acoustically transmissive adhesive disposed on the base in the cavity. The method further includes installing a removable adhesive liner to cover the acoustically transmissive adhesive. The method further includes packaging the cover with the liner in a container.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIGS. 2 and 3 illustrate an example cover for a hand held single enclosure ultrasound scanner;

FIGS. 4 and 5 illustrate an example needle guide of the cover;

FIG. 6 illustrates an example in which the cover includes an acoustically transmissive adhesive with a removable liner;

DETAILED DESCRIPTION

Figure 1:
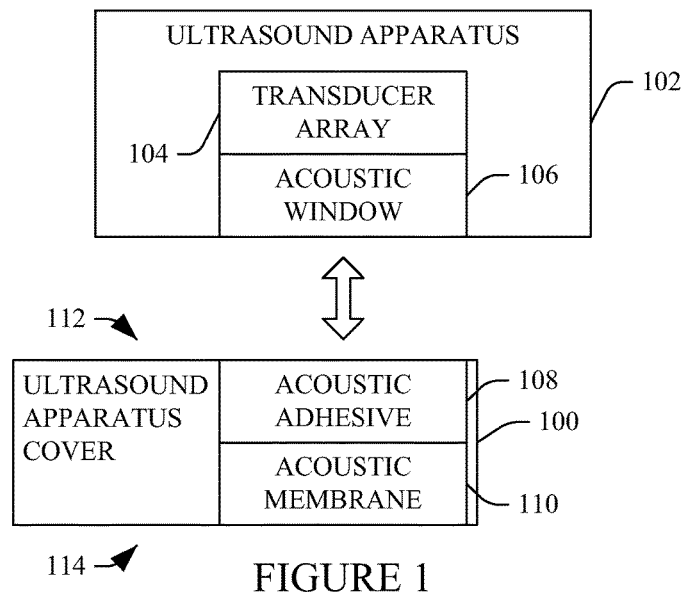
FIG. 1 schematically illustrates an example cover for an ultrasound apparatus.

FIG. 1 schematically illustrates an ultrasound apparatus cover 100 in connection with an ultrasound apparatus 102. In this example, the ultrasound apparatus 102 includes at least a transducer array 104 and an acoustic window/lens 106 located at a region of the ultrasound apparatus 102 configured to be placed in contact with an object or structure to scan a portion of the object or structure. As described in greater detail below, the ultrasound apparatus 102 may be part of a single enclosure hand held ultrasound scanner, a transducer probe configured to connect to a separate ultrasound console via a cable or the like, and/or other ultrasound apparatus 102.

The ultrasound apparatus cover 100 includes an acoustically transmissive membrane 110 and an acoustically transmissive adhesive 108, which is affixed thereto. The acoustically transmissive membrane 110 can include a plastic, a rubber and/or other material, including, but not limited to, a water based or an alcohol based liquid or gel, and/or a semi-rigid pad. In one embodiment, the acoustically transmissive membrane 110 provides a barrier that inhibits pathogens from migrating from one side of the membrane to the other side. The acoustically transmissive adhesive 108 is located in connection with a first side 112 of the ultrasound apparatus cover 100, and the acoustically transmissive membrane 110 is located adjacent thereto and in connection with a second opposing side 114 of the ultrasound apparatus cover 100, which opposes the first side 112. The acoustically transmissive adhesive 108 can be any type of adhesive with suitable acoustic coupling characteristics such as alcohol, water, oil, etc. based and/or other acoustically transmissive adhesive in the form of a liquid, a gel, a semi-rigid gel pad, a tape, a rigid material, and/or other form. The acoustically transmissive adhesive 108 and the acoustically transmissive membrane 110 are arranged with respect to each other in the ultrasound apparatus cover 100 such that the acoustically transmissive adhesive 108 and the acoustically transmissive membrane 110 are in mechanical contact and acoustically coupled.

The ultrasound apparatus cover 100 is generally rigid and pre-formed (e.g., thermo, injection mold, or otherwise formed) so that the first side geometrically conforms to a shape of at least a portion of the ultrasound apparatus 102 that includes the acoustic window/lens 106, before and after installing the cover 100 on the apparatus 102. In one instance, this includes configuring at least the shape of the ultrasound apparatus cover 100 so that the acoustically transmissive adhesive 108 and acoustically transmissive membrane 110 are positioned to align with the acoustic window 106 and hence the transducer array 104 when the cover 100 is installed on the apparatus 102. Suitable cover materials include plastic, cardboard, paper, metal, and/or other materials. In one instance, the material has a thickness in a range of about five thousandth of an inch to about forty thousandths of an inch such as twenty thousandths of an inch. Where the cover material includes a cardboard, paper or the like, the cover 100 can be laminated, coated and/or otherwise protected with a water resistant material. Optionally, the base, walls and acoustically transmissive membrane are monolithic and made of a thermoplastic material.

The acoustically transmissive adhesive 108, when placed in physical contact with the ultrasound apparatus 102, adheres to the acoustic window/lens 106 of the ultrasound apparatus 102, maintaining installation of the cover 100 with the apparatus 102. The acoustically transmissive adhesive 108 and the acoustically transmissive membrane 110 are arranged in the ultrasound apparatus cover 100 so that acoustically transmissive membrane 110 aligns with the acoustic window/lens 106 when the cover 100 is installed on the apparatus 102. In such a configuration, the acoustically transmissive adhesive 108 and the acoustically transmissive membrane 110 provide an acoustic medium between the transducer array 104 and the portion of the object or subject being scanned. In one instance, the acoustically transmissive adhesive 108 can be any suitable adhesive strength that allows the cover 100 to stay in place during use for scanning, but for purposes of disposal of the cover, is reasonably easily to release without damage to the ultrasound apparatus 102 or acoustic window/lens 106.

The ultrasound apparatus cover 100 may be disposable, cleanable, disinfectable, re-usable, and/or sterilizeable. Where the ultrasound apparatus cover 100 is disinfected and/or sterilized, the ultrasound apparatus cover 100 may provide a sonographer or other user of the ultrasound apparatus 102 a quick way of rendering the side 106 of the ultrasound apparatus 102 sterile. In this instance, the ultrasound apparatus cover 100 may also be packaged in a sterile package.

Optionally, the ultrasound apparatus cover 100 includes physical features for various functions such as to guide a needle for needle access procedures such as biopsies or peripheral IV line placements, to secure the ultrasound apparatus 102 in a desired position without human intervention, to apply an acoustic couplant between the cover 100 and the patient for scanning, and/or other physical features.

Figure 2:
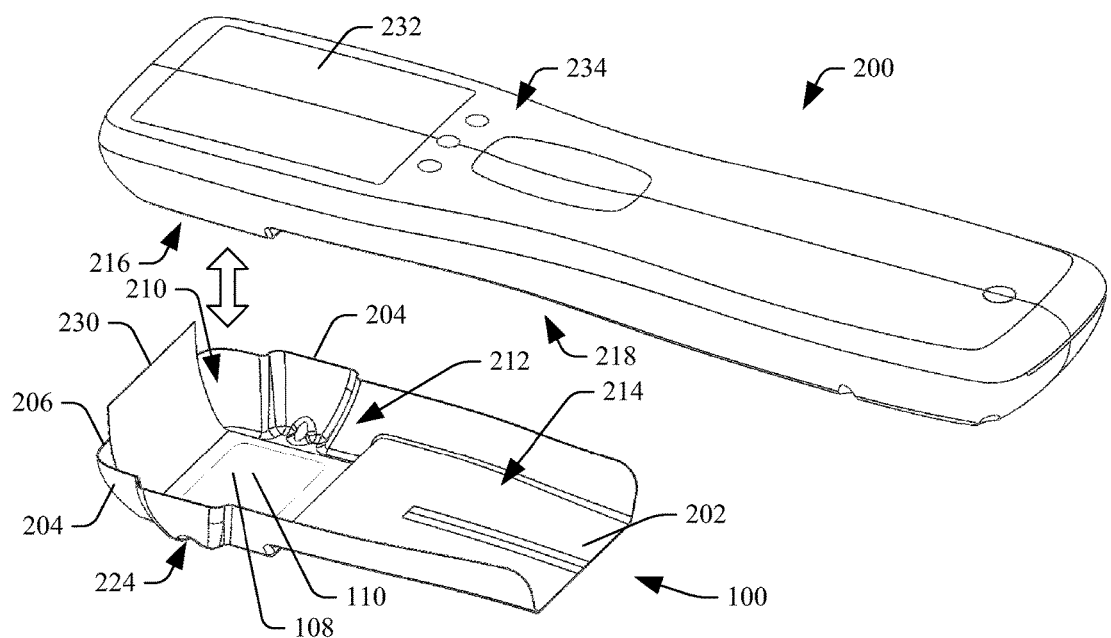

FIGS. 2 and 3 illustrate a non-limiting example of the ultrasound apparatus cover 100 where the ultrasound apparatus 102 includes an ultrasound scanner 200 configured as a hand held single enclosure. In FIG. 2, the cover 100 is not installed on the ultrasound scanner 200, and in FIG. 3 the cover 100 is installed on the ultrasound scanner 200.

Initially referring to FIG. 2, the cover 100 includes a base 202, first and second opposing side walls 204, and a front wall 206. The walls 204 and 206 protrude from the base 202 in a same direction, thereby forming an open cavity 210 defined by the base 202 and the walls 204 and 206, with an open side, which opposes the front wall 206, and an open side, which opposes the base 202.

A first portion 212 of the base 202 is located adjacent to the front wall 206 and a second portion 214 of the base 202 extends from the first portion 212 in a direction away from the front wall 206. The first portion 212 is recessed with respect to the second portion 212 and includes the acoustically transmissive membrane 110.

The first portion 212 has a geometrical shape that conforms substantially to a shape of a probe head 216 of the ultrasound scanner 200, which houses the transducer array 104 and acoustic window 106 (FIG. 1). The second portion 214 has a geometrical shape that conforms substantially to a shape of a handle portion 218 of the ultrasound scanner 200. In this embodiment, a length of the second portion 214 is less than a length of the handle portion 218. In other embodiments, the length of the second portion 214 can be larger or smaller, or the second portion 214 can be omitted.

A removable liner 230 is located in the cavity 210 and is used to cover the acoustically transmissive adhesive 108. The liner 230 is removed before installing the ultrasound apparatus cover 100 on the ultrasound scanner 200. In FIG. 2, the removable liner 230 is shown extending past the front wall 206 to enable easy grasping by the user. In this embodiment the liner 230 is completely removed from the cover 100. In other embodiments the liner could be folded to a position where it does not interfere with scanning with the ultrasound scanner 200.

FIG. 3 shows the cover 100 from a backside 302 of the base 202, which faces away from the cavity 210. As shown in FIG. 3, the walls 204 cover side walls 304 of the ultrasound scanner 200, the front wall 206 covers a front wall 306 of the ultrasound scanner 200, the first portion 212 of the base 202 rests against the probe head 216, the second portion 214 of the base 202 rests against the handle portion 218, and the acoustically transmissive membrane 110 adheres to the window portion 106 of the probe head 216 of the ultrasound scanner 200 via the acoustically transmissive adhesive 108.

In FIGS. 2 and 3, the cover 100 also includes a needle guide 224, which is located in connection with the walls 204. For sake of clarity, the needle guide 224 is discussed in connection with FIGS. 4 and 5, which respectively show a block diagram representation of the ultrasound apparatus cover 100 looking into the front wall 206 (FIG. 4) and looking into one of the side walls 204 (FIG. 5).

In FIGS. 4 and 5, the needle guide 224 includes a channel 402 which is configured to guide (e.g., provide a centerline), but not constrain, a needle 404 along a path for freehand or other insertion. The channel 402 is configured so that a tip region 406 of the needle 404 can be readily positioned in an imaging region 408 of the transducer array 104 between the transducer array 104 and a region 410 of a subject 412 where the needle is inserted. With a conventional single plane transducer, this may include guiding the needle 404 in the middle of elevation of the imaging region 408.

FIG. 4 shows a configuration with two needle guides 224, one on each of the two side walls 204. Other embodiments may include no, one, or more than two needle guides 224. In yet another embodiment, a needle guide 224 is additionally or alternatively located with respect to the front wall 206 and/or other location. Note that the size, shape and relative position of the components in FIGS. 4 and 5 are for explanatory purposes and are not limiting.

With continuing reference to FIGS. 2 and 3 and with reference to FIG. 6, a block diagram looking into the front wall 206 of the cover 100 and showing the acoustically transmissive adhesive 108 in the first portion 212 is illustrated. In this embodiment, the acoustically transmissive adhesive 108 is a pre-applied liquid or gel acoustic adhesive. In another instance, the acoustically transmissive adhesive 108 is a semi-rigid double-sided adhesive gel pad. In yet another instance, the acoustically transmissive adhesive 108 includes a plurality of sheets material. The liner 230 is shown removeably affixed over the acoustically transmissive adhesive 108 and is removed before installing the cover 100 on the ultrasounds scanner 200.

In FIGS. 2 and 3, the ultrasound scanner 200 is a hand held ultrasound scanner housed in a single enclosure. As such, the scanner 200 includes, in addition to the transducer array 104, a transducer array controller (not visible), an image processor (not visible), a display 232, and a user interface 234. The transducer array 104 includes a one-dimensional and/or a two-dimensional array of transducer elements arranged in a linear, curved, circular, or other manner, and is configured to acquire data for A-mode, B-mode, C-mode, etc. acquisitions, individually and in combination with color flow, Doppler flow, and/or other information.

The transducer array controller includes transmit and receive circuitry and a switch that switches between transmit and receive circuitry. Generally, the transmit circuitry controls actuation of the transducer elements, which allows for steering and/or focusing the transmitted beam from predetermined origins along the array and at predetermined angles, and the receive circuitry's various processes receive echoes and generates and outputs a processed signal. In one non-limiting instance, the receive circuitry delays and sums received echoes, generating a focused signal for a single line through a scanned region of interest. Other suitable processing includes, but is not limited to, spatial compounding, filtering (e.g., FIR, IIR, etc.), and/or other processing.

The image processor includes one or more processors that convert the signal from the transducer controller to generate data for display, for example, by converting the data to the coordinate system of the display. The display 232 can be used to present the converted data. By way of non-limiting example, in one mode, the display can present a plane of a vessel that is parallel to a bottom or transducer array and that shows the interior of the vessel along the long axis of the vessel, including a portion of the needle 404 within the displayed interior of the vessel, when the needle 404 is inserted into the vessel.

The user interface 234 includes various input and/or output devices for interacting with the transducer controller, for example, to select a data processing and presentation mode, a data acquisition mode, initiate scanning, etc. The user interface 234 may include various controls such as buttons, knobs, a keypad, a touch screen, etc. The user interface 234 may also include various types of visual (e.g., LCD, LED, etc.) and/or audible feedback.

Variations and/or other embodiments are contemplated.

Figure 12:
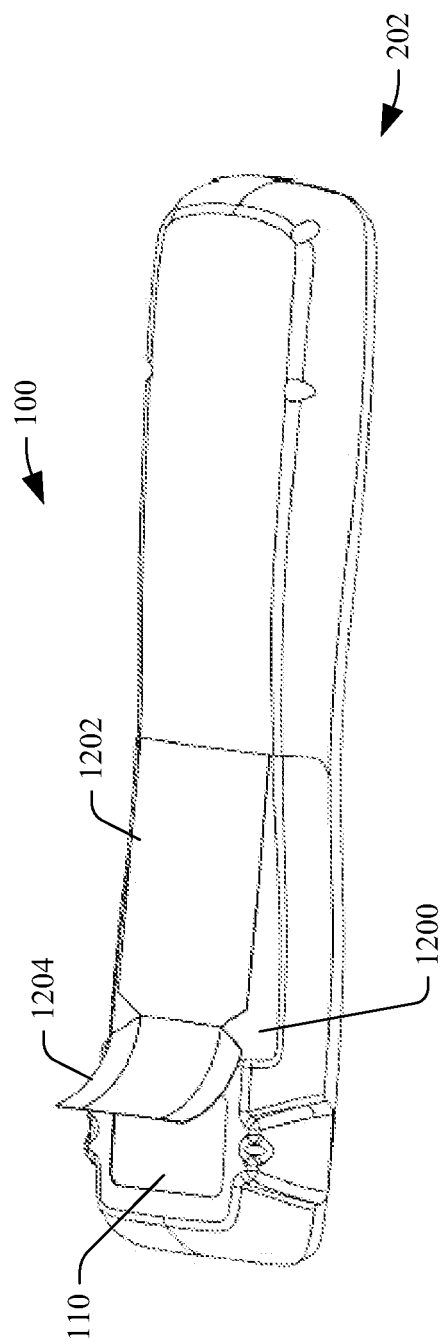
FIG. 12 illustrates an optional integrated gel dispense and an optional liner for covering the outside of the acoustically transmissive membrane.

FIG. 12 shows an embodiment in which the ultrasound apparatus cover 100 also includes a support region 1200 where a packet 1202 of acoustic coupling material can be removeably affixed. Various approaches can be used to affix the packet 1202 to the support region 1200. For example, an adhesive may be applied to the region 1200 and/or the packet 1202, and this adhesive can be used to affix the packet 1202 to the region 1200. In another example, the region 1200 may include a pocket in which the packet 1202 can be inserted into. Other approaches are also contemplated herein. In the illustrated embodiment, a removable tab 1204 is torn off and removed prior to the packet 1202 being squeezed to apply an acoustic coupling material to the exterior of acoustic membrane 110. In another embodiment, the support 1200 and packet 1202 are omitted, and an acoustic couplant such as a hydrogel pad is integrated with the membrane 110.

In another embodiment, the removable tab 1204 additionally comprises a removable sterile liner 1204 that covers surfaces that are intended to remain sterile such as the acoustic membrane 110 of the side that contacts the patient. The liner 1204 can be removed before, during or after installing the ultrasound apparatus cover 100 on the ultrasound scanner 200, but before scanning. In FIG. 12, the removable liner 1204 is shown partially folded back and partially removed. The liner 1204 can be completely removed from the cover 100 or folded to a position where it does not interfere with scanning with the ultrasound scanner 200. In another embodiment this sterile liner 1204 may be a separate feature from the packet 1202 and/or there may be no packet.

Figure 7:
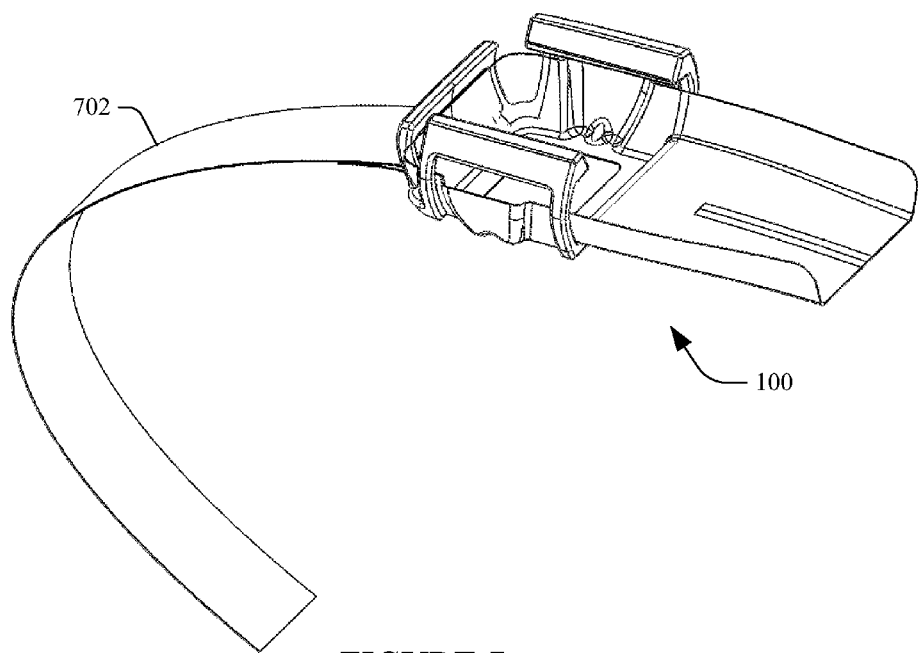
FIGS. 7 and 8 illustrate a variation of the cover of FIGS. 2 and 3 in which the cover includes a strap for holding the transducer in place on a patient.
Figure 8:
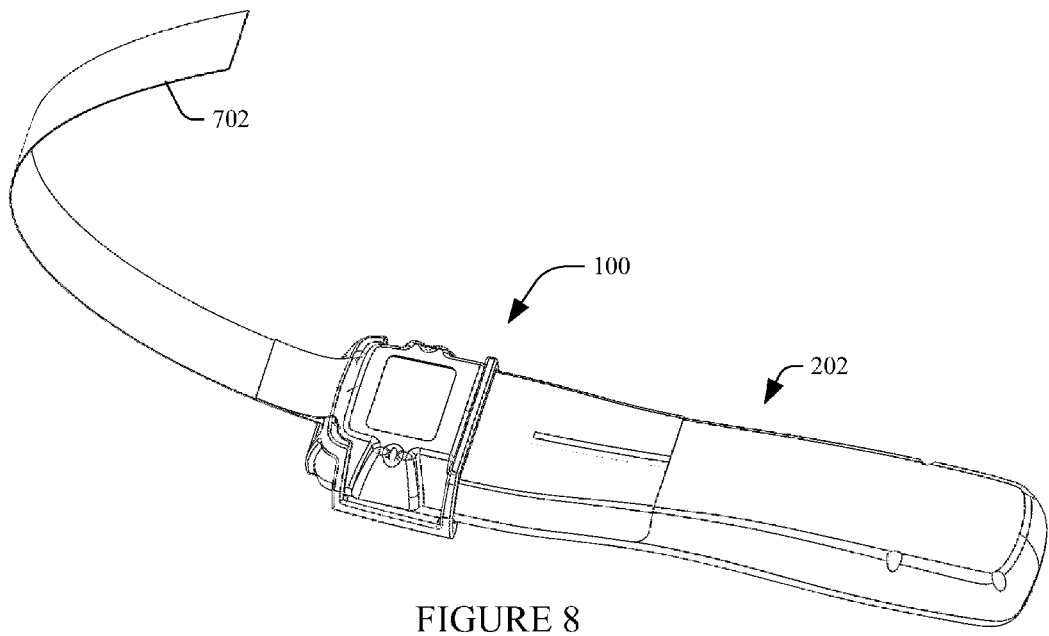

FIGS. 7 and 8 show a variation in which the ultrasound apparatus cover 100 further includes a strap 702. In this example, the strap 702 is affixed at the front wall 206 of the cover 100. In other embodiments, the strap 702 can be elsewhere affixed to the cover 100. The strap 702 can include various materials such as rubber, plastic, leather, etc. The strap 702 can be used for various reasons. For example, in one instance the strap 702 is used to secure the ultrasound scanner 200 in position with respect to the region of the subject or object being scanned. This may include wrapping or tying the strap around a fixture or device in the examination room. In this manner, the user of the ultrasound scanner 200 does not have to hold the ultrasound scanner 200 in position. This allows, for example, the user of the ultrasound scanner 200 to free up his hands, for example, so that the user can use both hands to insert a needle into the subject or object.

Figure 9:
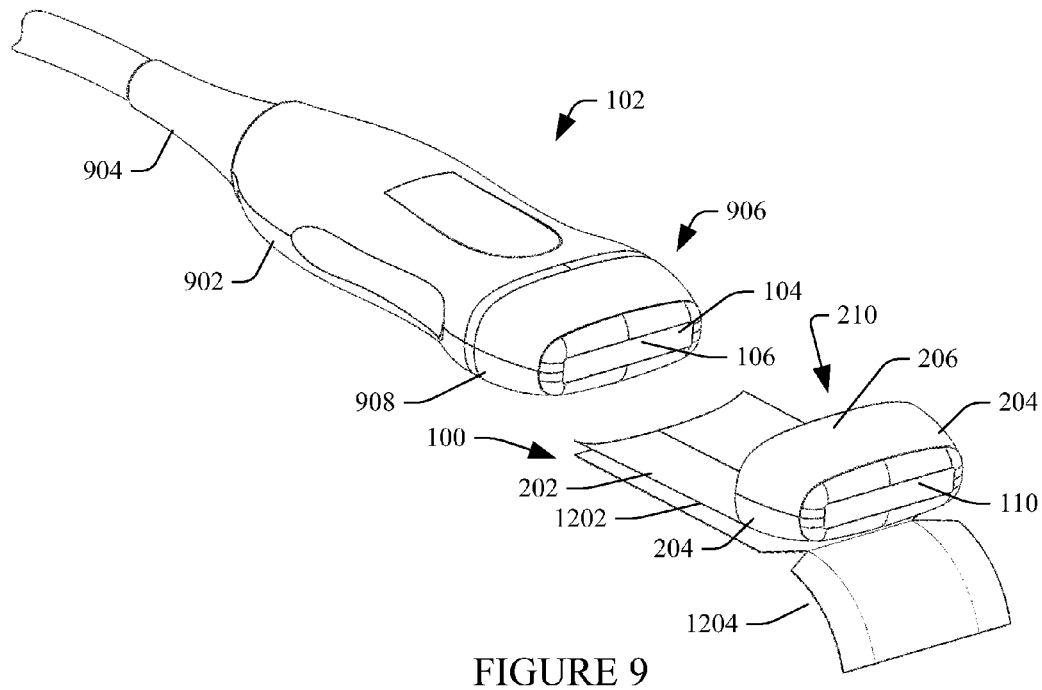
FIGS. 9 and 10 illustrate an example cover for a probe configured to be connected to an ultrasound scanner console via a cable.
Figure 10:
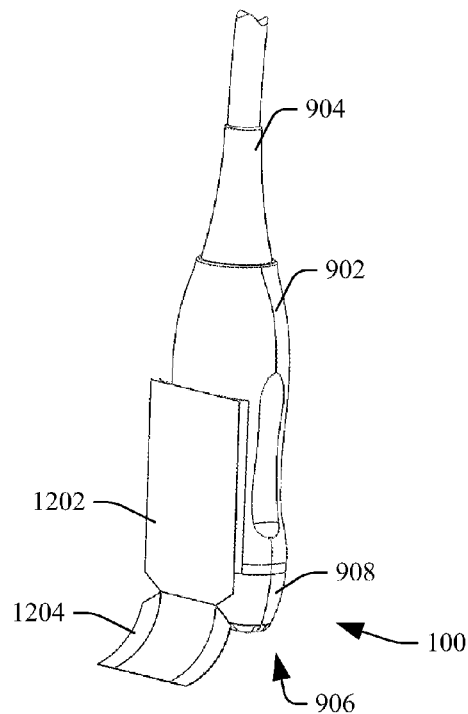

FIGS. 9 and 10 illustrate a non-limiting example in which the ultrasound apparatus 102 is a conventional ultrasound probe 902 that connects to a separate ultrasound console via an electrical cable interface 904. This cable interface may or may be detachable from the console via an electrical connector. In this instance, the console includes the transducer array controller, the image processor, the display and a user interface. With the illustrated probe 902, the transducer array 104 is located at an end 906 of the probe head 908.

In this embodiment, the second portion 214 of the base 202 extends in the same direction as the walls 204 and 206, and the open cavity 210 is defined by the first and second portions 214 and 214 of the base 202 and the walls 204 and 206, with only the open side that opposes the base 202. Likewise, the cover 100 is rigid and the cavity 210 is pre-formed and geometrically configured based on the geometry of the probe head 908. Furthermore, the acoustically transmissive adhesive 108 (not visible) is in the cavity 210 next to the acoustically transmissive membrane 110 and adheres to the acoustic window 104 when the cover 100 is installed on the probe 902, maintaining installation.

In this embodiment, the cover 100 also includes the packet of acoustic material 1202 affixed thereto which is discussed at least in connection with FIGS. 2 and 3. In another instance, the packet 1204 is omitted. Unlike cover 100 in FIGS. 2 and 3, the cover 100 in this embodiment does not include the needle guide 224 or the strap 702. However, in other embodiments, the cover 100 for the probe 902 also includes at least one of needle guide 224 or the strap 702. Additionally or alternatively, a separate needle guide can be employed with the probe 902.

Although two types of ultrasound apparatuses 102 are shown (FIGS. 2 and 3 and FIGS. 9 and 10), it is to be understood that other types of ultrasound apparatuses 102 are also contemplated herein. In such other instance, the apparatus cover 100 can be configured based on the geometry of the particular ultrasound apparatus 102, in accordance to the description herein and/or variants thereof. Moreover, in such instances one or more of the features (e.g., needle guide, strap, acoustic couplant dispenser, etc.) described herein can be included.

Figure 11:
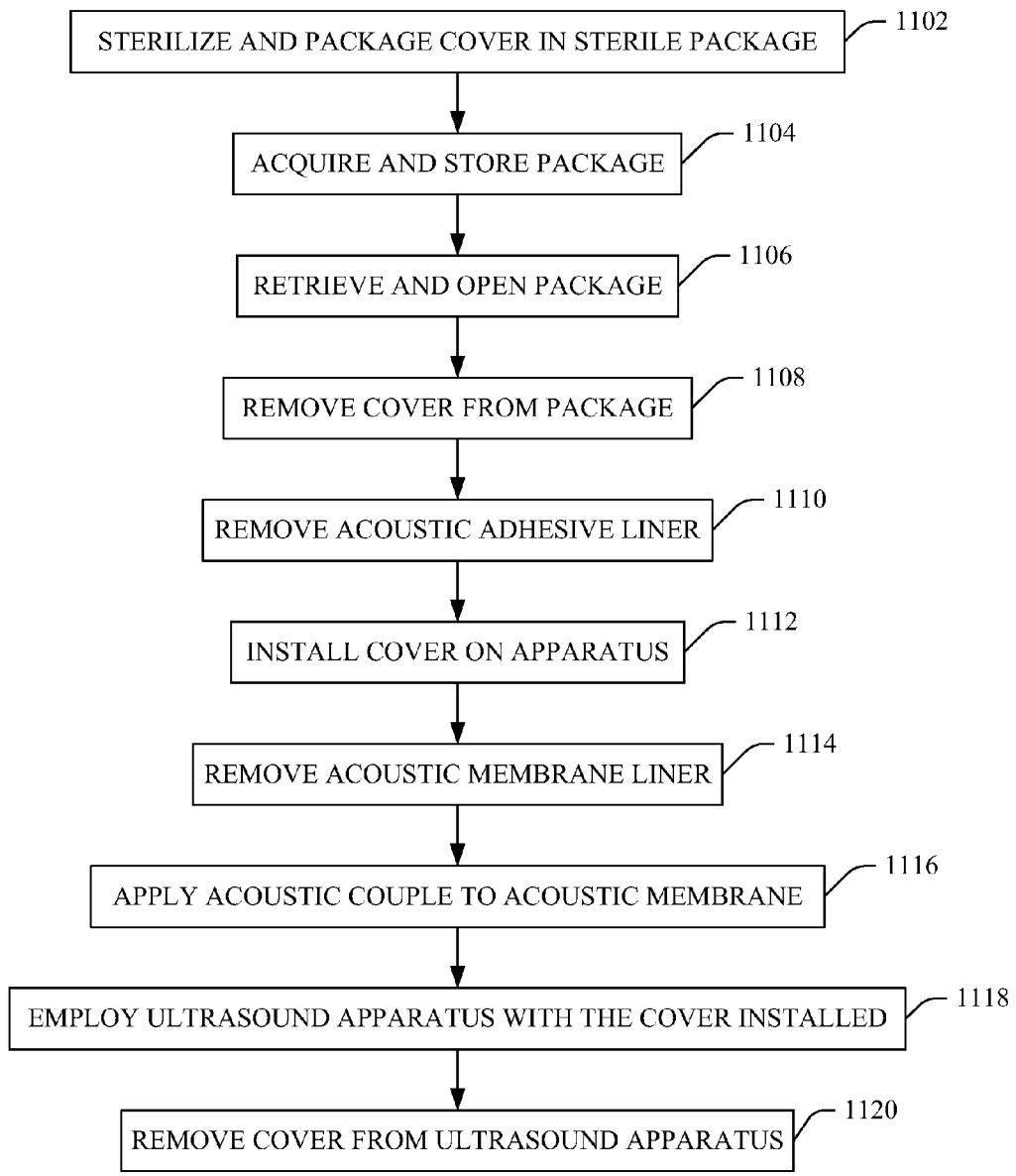
FIG. 11 illustrates an example method for the cover.

It is to be appreciated that the cover 100 can be sterilized and packaged for use in sterile environments and used in such an environment. FIG. 11 illustrates an example method of this.

It is to be understood that the following acts are provided for explanatory purposes and are not limiting. As such, one or more of the acts may be omitted, one or more acts may be added, one or more acts may occur in a different order (including simultaneously with another act), etc.

At 1102, the cover 100 is sterilized and placed in sterilizeable package, which is sealed and sterilized. This can be achieved by a manufacturer and/or any appropriate sterilization method (e.g., EtO, Gamma Ray, etc.).

At 1104, the package is acquired by a health care facility and stored in a location that won't compromise the sterility of the cover 100.

At 1106, the package is retrieved and opened in a sterile environment.

At 1108, the cover 100 is removed from the sterile package. This can be done via authorized personnel wearing sterile clothes, where the cover 100 is handled so as not to breach its sterility.

At 1110, the inside adhesive liner 230 is removed. In instances where the cover 100 does not include the liner 230, this act is omitted.

At 1112, the cover 100 is installed on the ultrasound apparatus 102. As described herein, this includes physically contacting the acoustically transmissive adhesive 108 with the acoustic window 106 of the ultrasound apparatus 102, where the acoustically transmissive adhesive 108 holds the cover 100 in place.

At 1114, the outside acoustically transmissive membrane liner 1204 is removed. In instances where the cover 100 does not include the liner 1204, this act is omitted.

At 1116, the packet 1202 is used to apply a sterile acoustic couplant on the acoustically transmissive membrane 110. In instances where the cover 100 does not include the packet 1202, the sterile acoustic couplant can be manually applied from a separate bottle/packet to the acoustically transmissive membrane 110 and/or object or subject.

At 1118, the ultrasound apparatus 102 with the cover 100 installed thereon is used to perform an ultrasound procedure.

At 1120, subsequent to imaging with the apparatus 102, the cover 100 is removed from the ultrasound apparatus 102 and discarded or alternatively cleaned, disinfected, sterilized, etc.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A rigid and pre-formed ultrasound apparatus cover for a hand held single enclosure ultrasound scanner that includes a probe head with at least a transducer array and a corresponding acoustic window, an image processor, a user interface and a display, the rigid and pre-formed ultrasound apparatus cover comprising:
a base:
first and second opposing side walls: and
a front wall,
wherein the first, second and front walls protrude from the base in a same direction forming an open cavity defined by the base and the first, second and front walls, with an open side, which opposes the front wall, and an open side, which opposes the base,
wherein the base includes a first portion adjacent to the front wall and a second portion extending from the first portion in a direction away from the front wall,
wherein the front wall includes a first end and a second opposing end,
wherein the first side wall has a first end and is transverse to the front wall, and the first end of the first side wall meets the first end of the front wall, and the second side wall has a first end and is transverse to the front wall, the first end of the second side wall meets the second end of the front wall,
wherein at least one of the first or second walls includes at least one channel configured to guide a needle being inserted into a region of an object or subject;
an acoustically transmissive membrane with first and second opposing sides, wherein the acoustically transmissive membrane is disposed on the first portion of the base; and
an acoustically transmissive adhesive disposed on the acoustically transmissive membrane in the open cavity.

2. The rigid and pre-formed ultrasound apparatus cover of claim 1, wherein the acoustically transmissive adhesive provides an acoustic medium for transmission of ultrasound signals between the acoustic window of the hand held single enclosure ultrasound scanner and the acoustically transmissive membrane of the rigid and pre-formed ultrasound apparatus cover.

3. The rigid and pre-formed ultrasound apparatus cover of claim 1, wherein the acoustically transmissive membrane includes a plastic or rubber film.

4. The rigid and pre-formed ultrasound apparatus cover of claim 1, wherein the acoustically transmissive membrane includes one of a water based or an alcohol based liquid or gel.

5. The rigid and pre-formed ultrasound apparatus cover of claim 1, wherein the acoustically transmissive membrane includes a semi-rigid pad.

6. The rigid and pre-formed ultrasound apparatus cover of claim 1, wherein the first portion of the base is recessed in the base relative to the second portion of the base.

7. The rigid and pre-formed ultrasound apparatus cover of claim 1, wherein the base and the first and second walls are configured to receive the probe head of the hand held single enclosure ultrasound apparatus.

8. The rigid and pre-formed ultrasound apparatus cover of claim 7, wherein the second portion of the base includes a non-acoustically transmissive membrane region and is configured to receive a handle portion of the hand held single enclosure ultrasound apparatus.

9. The rigid and pre-formed ultrasound apparatus cover of claim 1, wherein the front, the first, and the second walls form a closed wall around the acoustically transmissive membrane.

10. The rigid and pre-formed ultrasound apparatus cover of claim 1, wherein the channel guides the needle through a region located between the acoustically transmissive membrane and the region of an object or subject.

11. The rigid and pre-formed ultrasound apparatus cover of claim 1, wherein the base includes a cardboard or paper material.

12. The rigid and pre-formed ultrasound apparatus cover of claim 11, wherein the base material is laminated or coated with a water resistant material.

13. The rigid and pre-formed ultrasound apparatus cover of claim 1, wherein the base includes an injection molded material or thermoformed thermoplastic material.

14. The rigid and pre-formed ultrasound apparatus cover of claim 1, wherein the base, the front, first and second walls, and the acoustically transmissive membrane are monolithic and comprise a thermoplastic material.

15. The rigid and pre-formed ultrasound apparatus cover of claim 1, further comprising:
an adhesive liner that is removeably affixed next to and covers a surface of the acoustically transmissive adhesive, and the adhesive liner faces towards the acoustically transmissive membrane and into the cavity.

16. The rigid and pre-formed ultrasound apparatus cover of claim 1, wherein the acoustically transmissive adhesive is releasable from the hand held single enclosure ultrasound scanner after use.

17. The rigid and pre-formed ultrasound apparatus cover of claim 1, further comprising:
a strap configured to be secured to a static structure to maintain the rigid and pre-formed ultrasound apparatus cover, and hence the hand held single enclosure ultrasound scanner, at a static position without human intervention.

18. The rigid and pre-formed ultrasound apparatus cover of claim 1, further comprising:
a support region configured to support a container of an acoustic coupling medium.

19. The rigid and pre-formed ultrasound apparatus cover of claim 18, wherein the container is configured to dispense the acoustic coupling medium onto the acoustically transmissive membrane.

20. The rigid and pre-formed ultrasound apparatus cover of claim 1, wherein the rigid and pre-formed ultrasound apparatus cover is a sterilized rigid and pre-formed ultrasound apparatus cover and is disposed in a sterile kit.

21. The rigid and pre-formed ultrasound apparatus cover of claim 1, wherein the acoustically transmissive membrane provides a barrier that inhibits pathogens from migrating from the first to the second opposing sides.

* * * * *